United States Patent
Blitzer et al.

(10) Patent No.: US 6,893,656 B2
(45) Date of Patent: May 17, 2005

(54) ATHLETIC PATCH

(75) Inventors: Andrew Blitzer, New York, NY (US); Terry Pretorius, New York, NY (US)

(73) Assignee: Vita-Patch, LLC, Milton, MA (US)

( * ) Notice: Subject to any disclaimer, the term of this patent is extended or adjusted under 35 U.S.C. 154(b) by 0 days.

(21) Appl. No.: 10/271,827

(22) Filed: Oct. 15, 2002

(65) Prior Publication Data

US 2003/0054026 A1 Mar. 20, 2003

Related U.S. Application Data

(63) Continuation of application No. 09/452,517, filed on Dec. 1, 1999, now Pat. No. 6,475,514.
(60) Provisional application No. 60/110,771, filed on Dec. 3, 1998.

(51) Int. Cl.[7] .......................... A61F 13/00; A61L 15/16
(52) U.S. Cl. ...................................... 424/449; 424/448
(58) Field of Search .............................. 424/449, 448

(56) References Cited

U.S. PATENT DOCUMENTS

| | | | |
|---|---|---|---|
| 3,699,963 A | 10/1972 | Zaffaroni | 128/268 |
| 4,025,650 A | 5/1977 | Gans et al. | 424/319 |
| 4,322,407 A | 3/1982 | Ko | 424/128 |
| 4,329,999 A | 5/1982 | Phillips | 128/760 |
| 4,474,570 A | 10/1984 | Ariura et al. | 604/20 |
| 4,595,011 A | 6/1986 | Phillips | 128/636 |
| 4,604,286 A | 8/1986 | Kawajiri | 424/149 |
| 4,640,689 A | 2/1987 | Sibalis | 604/20 |
| 4,666,441 A | 5/1987 | Andriola et al. | 604/897 |
| 4,687,782 A | 8/1987 | Brantman | 514/561 |
| 4,704,282 A | 11/1987 | Campbell et al. | 424/449 |
| 4,732,153 A | 3/1988 | Phillips | 128/636 |
| 4,746,515 A | 5/1988 | Cheng et al. | 424/449 |
| 4,764,164 A | 8/1988 | Sasaki | 604/20 |
| 4,865,848 A | 9/1989 | Cheng et al. | 424/449 |
| 4,871,550 A | 10/1989 | Millman | 424/601 |
| 4,876,278 A | 10/1989 | Taylor et al. | 514/494 |
| 4,878,892 A | 11/1989 | Sibalis et al. | 604/20 |
| 4,892,737 A | 1/1990 | Bodor et al. | 424/449 |
| 4,900,555 A | 2/1990 | Cheng et al. | 424/449 |
| 4,919,648 A | 4/1990 | Sibalis | 604/20 |
| 4,921,475 A | 5/1990 | Sibalis | 604/20 |
| 4,940,456 A | 7/1990 | Sibalis et al. | 604/20 |
| 4,940,586 A | 7/1990 | Cheng et al. | 424/464 |
| 4,981,687 A | 1/1991 | Fregly et al. | 424/439 |
| 5,032,109 A | 7/1991 | Sibalis | 604/20 |
| 5,034,192 A | 7/1991 | Wrighton et al. | 422/82.02 |
| 5,087,240 A | 2/1992 | Sibalis | 604/20 |
| 5,088,978 A | 2/1992 | Hillman et al. | 604/20 |
| 5,140,985 A | 8/1992 | Schroeder et al. | 128/632 |
| 5,156,846 A | 10/1992 | Petersen et al. | 424/443 |
| 5,164,416 A | 11/1992 | Nagai et al. | 514/763 |
| 5,217,997 A | 6/1993 | Levere et al. | 514/565 |
| 5,224,927 A | 7/1993 | Tapper | 604/20 |
| 5,227,157 A | 7/1993 | McGinity et al. | 424/78.02 |
| 5,250,023 A | 10/1993 | Lee et al. | 604/20 |
| 5,306,503 A | 4/1994 | Muller et al. | 424/449 |
| 5,354,321 A | 10/1994 | Berger | 607/75 |
| 5,356,632 A | 10/1994 | Gross et al. | 424/449 |

(Continued)

FOREIGN PATENT DOCUMENTS

| | | |
|---|---|---|
| EP | 0 595 005 A1 | 5/1994 |
| EP | 0 776 677 A2 | 6/1997 |
| WO | WO 97/04832 | 2/1997 |

*Primary Examiner*—Thurman K. Page
*Assistant Examiner*—Isis Ghali
(74) *Attorney, Agent, or Firm*—Wolf, Greenfield & Sacks, P.C.

(57) ABSTRACT

The present invention relates to patches for the administration of an athletic supplement to subjects engaged in rigorous exercise or heavy outdoor work. The invention also relates to methods of administering nutrients to subjects using the patch of the invention.

3 Claims, 1 Drawing Sheet

| Patent No. | Date | Inventor | Class |
|---|---|---|---|
| 5,397,786 A | 3/1995 | Simone | 514/300 |
| 5,403,275 A | 4/1995 | Phipps | 604/20 |
| 5,405,614 A | 4/1995 | D'Angelo et al. | 424/449 |
| 5,413,794 A | 5/1995 | Suzuki et al. | 424/449 |
| 5,415,629 A | 5/1995 | Henley | 604/20 |
| 5,420,107 A | 5/1995 | Brooks | 514/2 |
| 5,421,816 A | 6/1995 | Lipkovker | 604/20 |
| 5,422,352 A | 6/1995 | Astrup | |
| 5,458,569 A | 10/1995 | Kirk, III et al. | 604/20 |
| 5,460,605 A | 10/1995 | Tuttle et al. | 604/67 |
| 5,462,743 A | 10/1995 | Turner et al. | 424/448 |
| 5,465,713 A | 11/1995 | Schoendorfer | 128/632 |
| 5,466,465 A | 11/1995 | Royds et al. | 424/449 |
| 5,473,966 A | 12/1995 | Cordon | 83/56 |
| 5,478,568 A | 12/1995 | Takayasu et al. | 424/449 |
| 5,496,827 A | 3/1996 | Patrick | 514/310 |
| 5,516,526 A | 5/1996 | da la Torre | 424/449 |
| 5,527,797 A | 6/1996 | Eisenberg et al. | 514/231.2 |
| 5,536,263 A | 7/1996 | Rolf et al. | 604/307 |
| 5,543,405 A | 8/1996 | Keown et al. | 514/188 |
| 5,601,839 A | 2/1997 | Quan et al. | 424/448 |
| 5,605,536 A | 2/1997 | Sibalis | 604/20 |
| 5,605,701 A | 2/1997 | Bymaster et al. | 424/448 |
| 5,607,691 A | 3/1997 | Hale et al. | 424/449 |
| 5,613,958 A | 3/1997 | Kochinke et al. | 604/307 |
| 5,641,504 A | 6/1997 | Lee et al. | 424/447 |
| 5,643,596 A | 7/1997 | Pruss et al. | 424/426 |
| 5,645,849 A | 7/1997 | Pruss et al. | 424/426 |
| 5,650,156 A | 7/1997 | Grinstaff | |
| 5,651,768 A | 7/1997 | Sibalis | 604/20 |
| 5,656,286 A | 8/1997 | Miranda et al. | 424/449 |
| 5,662,925 A | 9/1997 | Ebert et al. | 424/447 |
| 5,662,926 A | 9/1997 | Wick et al. | 424/448 |
| 5,665,378 A | 9/1997 | Davis et al. | 424/448 |
| 5,667,487 A | 9/1997 | Henley | 604/20 |
| 5,667,798 A | 9/1997 | Royds et al. | 424/449 |
| 5,676,969 A | 10/1997 | Wick et al. | 424/448 |
| 5,679,373 A | 10/1997 | Wick et al. | 424/448 |
| 5,681,568 A | 10/1997 | Goldin et al. | 424/184.1 |
| 5,683,711 A | 11/1997 | Fischer et al. | 424/449 |
| 5,683,712 A | 11/1997 | Cavazza | 424/449 |
| 5,683,713 A | 11/1997 | Blank et al. | 424/449 |
| 5,688,232 A | 11/1997 | Flower | 604/20 |
| 5,693,335 A | 12/1997 | Xia et al. | 424/448 |
| 5,714,519 A | 2/1998 | Cincotta et al. | 514/616 |
| 5,716,976 A | 2/1998 | Bernstein | 514/386 |
| 5,731,303 A | 3/1998 | Hsieh | 514/183 |
| 5,741,510 A | 4/1998 | Rolf et al. | 424/448 |
| 5,756,469 A | 5/1998 | Beale | 514/23 |
| 5,770,219 A | 6/1998 | Chiang et al. | 424/448 |
| 5,997,904 A | 12/1999 | Magdassi | |
| 6,475,514 B1 | 11/2002 | Blitzer | |

ATHLETIC PATCH

RELATED APPLICATIONS

This application is a continuation of prior U.S. application Ser. No. 09/452,517, filed on Dec. 1, 1999, now U.S. Pat. No. 6,475,514 and entitled "Athletic Patch," which is now allowed and which claims priority under 35 USC §119 to U.S. Provisional Application Ser. No. 60/110,771 filed Dec. 3, 1998, and entitled "Athletic Patch".

FIELD OF THE INVENTION

The present invention relates to patches for the administration of an athletic supplement to subjects engaged in rigorous exercise or heavy outdoor work. The invention also relates to methods of administering nutrients to subjects using the patch of the invention.

BACKGROUND OF THE INVENTION

Strenuous exercise that occurs during athletic events, such as marathons, causes trauma to the body. For instance, exercise causes the release of adrenocorticotropin (ACTH) which leads to the increased production and release of cortisol. High levels of cortisol cause the release of amino acids from muscle tissue and prevent absorption of glucose, causing the catabolic breakdown of muscle tissue. Many cortisol blockers can be used to prevent the catabolic breakdown of muscle tissue, including leucine, antioxidants, and glutamic acid.

Exercise also causes the loss of many nutrients. Many types of sports drinks have been developed and marketed with the intent to replace the nutrients lost during athletic events. These sports drinks, such as Gatorade utilize sugar and electrolytes with water to prevent loss of carbohydrates and water during exercise. In general these drinks include sugars, electrolytes, vitamins, minerals, amino acids, and other important nutrients. In some cases pyruvate has also been added to such drinks to improve performance and help to prevent the detrimental breakdown of protein as an energy source.

There are several types of sports drinks currently available. One type includes sugar and water, such as the drink marketed by Coca-Cola Company under the trade name "Max". Max contains a 5% solution of dextrose and maltodextrin. Other types of sports drinks include sugar, water and electrolytes, and in some cases vitamins. These types of drinks include Gatorade and Exceed. Gatorade, for instance, contains a 6% solution of sucrose and glucose, 220 mg of sodium and 50 mg of potassium per serving and some vitamin C. Even other drinks, such as Body Fuel 450, include sugar, water, electrolytes, vitamins and minerals. The most comprehensive of these drinks include the following ingredients:

1–100 g of at least 1 carbohydrate,

2–2500 mg of at least 1 electrolyte, 0.1–750 mg of at least 1 ammonia neutralizer, at least one energy enhancer, preferably selected 2000 mg vitamins of the vitamin B group, 10–40,000 mg L-carnitin, creatine and choline, and 1–100 mg branched chain amino acids, at least one antioxidant, preferably selected from β-carotene in a quantity of 2 μg–200 μg, vitamin C in a quantity of 10–250 mg, vitamin E in a quantity of 8–30 l. selenium in a quantity of 10–300 μg, 1–30 mg of at least 1 membrane stabilizer, 1–200 μg of at least 1 neuromuscular enhancer, and water in a quantity at least sufficient to provide a solution such that each of the above components are substantially dissolved and which is ready for consumption by drinking.

One problem with all of these drinks is that they are dependent upon gastrointestinal absorption in order for the nutrients to be administered and disseminated among the body. Under conditions of dehydration and electrolyte imbalance, normal absorption may not occur. Additionally, not all of the nutrients are metabolized at the same rate, and thus may not be effectively used during the period of the athletic event.

Much research has indicated that amino acids of the branched chain type including valine, leucine and isoleucine, are essential to maintaining and repairing cellular integrity during athletic stress. One problem with these amino acids, however, is their adverse palatability, making it difficult to incorporate them into sports drinks.

Additionally, the sports drinks require that energy be utilized to digest and process the nutrients therein. This process requires the use of energy which could otherwise be used to fuel the muscles and provide energy to the athlete.

SUMMARY OF THE INVENTION

The present invention relates to methods and products for replenishing nutrients and supplying additional components to a subject involved in strenuous exercise which avoids many of the limitations associated with sports drinks.

The invention in one aspect is a patch for administering nutrients utilized during exercise and other periods of high energy consumption. The patch is particularly useful for athletes during sporting events such as marathons in which the nutrients are used rapidly by the body. The nutrients are delivered from the patch directly to the blood stream where they can supply the necessary energy or maintenance of homeostatic conditions in the body. There is no need for the nutrients to pass through the gastrointestinal tract where absorption would be a limiting factor.

In one aspect the invention is an article of manufacture including a patch for topical delivery of an athletic supplement to a subject which includes at least two compounds selected from the group consisting of a carbohydrate, an electrolyte, a vitamin, an amino acid, chromium, and a mineral. Preferably the patch includes at least three of these compounds. Preferably the athletic supplement includes at least one carbohydrate.

In one embodiment the athletic supplement includes an electrolyte. In another embodiment the athletic supplement includes a vitamin. In another embodiment the athletic supplement includes an amino acid. In yet another embodiment the athletic supplement includes chromium. According to another embodiment the athletic supplement includes an energy enhancer. Preferably, the athletic supplement includes a vitamin, an amino acid, chromium, and an energy enhancer.

The patch may include many different concentrations of the components of the athletic supplement. In a preferred embodiment the athletic supplement is at least 1 to 100 grams of carbohydrate and 2 to 2500 milligrams of electrolyte.

In addition to the above-described components, the athletic supplement may also include at least one of the following compounds: sodium chloride, potassium chloride, anhydrous magnesium sulphate, dodecahydrated disodium hydrogen phosphate, hydrated sodium dihydrogen phosphate, dextrose, sucrose, ascorbic acid, pyridoxine hydrochloride, sodium citrate, and citric acid.

The patch may be any type of conventional patch, such as a transdermal patch, a sublingual patch, or a buccal patch. Preferably, the patch is a transdermal patch for administering the athletic supplement to skin of the subject. In a preferred embodiment the patch includes a permeation enhancing amount of at least one skin permeation enhancer. Preferably the skin permeation enhancer is selected from the group consisting of menthol, eucalyptol, glyceryl monostearate and d-limonene. In another preferred embodiment the patch is a sublingual patch.

According to another aspect of the invention an article of manufacture is provided. The article of manufacture includes a patch for topically administering an athletic supplement to a subject, wherein the device is formulated to deliver the athletic supplement within 24 hours. In one embodiment the patch is a transdermal-patch for administering the athletic supplement to skin of the subject.

The patch may be designed to release the athletic supplement over any period of time within 24 hours. In one embodiment the patch is formulated for administering the athletic supplement within 12 hours. In another embodiment, the patch is formulated for administering the athletic supplement within 6 hours. In yet another embodiment the patch is formulated for administering the athletic supplement within 4 hours.

According to another embodiment the patch includes a permeation enhancing amount of at least one skin permeation enhancer selected from the group consisting of menthol, eucalyptol, glyceryl monostearate and d-limonene.

Preferably the athletic supplement includes at least one carbohydrate.

In one embodiment the athletic supplement includes an electrolyte. In another embodiment the athletic supplement includes a vitamin. In another embodiment the athletic supplement includes an amino acid. In yet another embodiment the athletic supplement includes chromium. According to another embodiment the athletic supplement includes an energy enhancer. Preferably, the athletic supplement includes a vitamin, an amino acid, chromium, and an energy enhancer.

According to yet another aspect the invention is a method of administering nutrients to a subject. The method includes the step of transdermally administering an athletic supplement to a subject while the subject is undergoing a physical activity to provide the subject with nutrition and energy required to perform the physical activity. Preferably, the athletic supplement is administered using the patch of the invention described above.

Preferably the athletic supplement includes at least one carbohydrate.

In one embodiment the athletic supplement includes an electrolyte. In another embodiment the athletic supplement includes a vitamin. In another embodiment the athletic supplement includes an amino acid. In yet another embodiment the athletic supplement includes chromium. According to another embodiment the athletic supplement includes an energy enhancer. Preferably, the athletic supplement includes a vitamin, an amino acid, a mineral, and an energy enhancer.

In another aspect, the invention is article of manufacture which is a patch for topical delivery of an athletic supplement to a subject which includes at least an amino acid, chromium, and a vitamin. Preferably the vitamin is vitamin B-15. In one embodiment, the patch is a transdermal patch.

Each of the limitations of the invention can encompass various embodiments of the invention. It is, therefore, anticipated that each of the limitations of the invention involving any one element or combinations of elements can be included in each aspect of the invention.

DETAILED DESCRIPTION OF THE INVENTION

Figure 1:
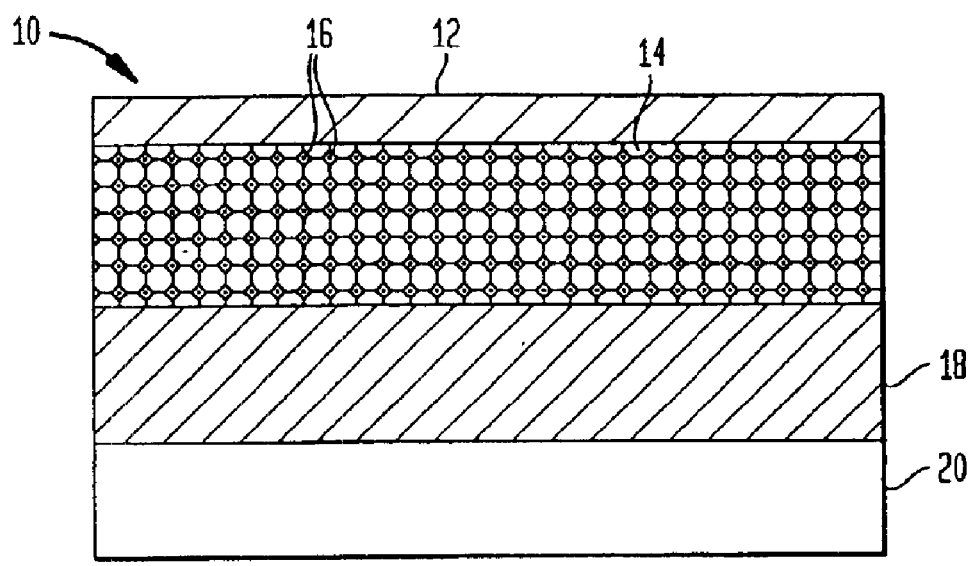
FIG. 1 depicts a transdermal patch having a diffusion layer matrix.

The invention relates to methods and products for delivering nutrients to a subject involved in rigorous exercise. In one aspect the invention is a delivery system for the delivery of nutrients through the skin or mucosal membrane of a subject during a defined period of time during which the subject is involved in a physical activity and which includes at least two compounds selected from the following compounds: a carbohydrate, a vitamin, an amino acid, chromium, a mineral, and an electrolyte.

The delivery of an athletic supplement using a patch offers several advantages over traditional delivery methods. For instance, the patch avoids gastrointestinal metabolism of the athletic supplement, reduces first pass effects and may if desirable provide a longer course of release of the components of the athletic supplement than traditional methods such as the use of sports drinks.

During strenuous exercise, the ability of the body to dissipate metabolically produced heat depends on the subject's ability to form and vaporize sweat. There is a progressive increase in body temperature as the ability to sweat decreases. In addition to the increased body temperature and perspiration, exercise also causes an increase in pulse rate, a decrease in the blood volume and biochemical changes associated with the metabolism of compounds to produce energy, such as glucose utilization. During extreme exercise, carbohydrates are increasingly used as the source of readily available energy, as opposed to fat metabolism. The body will continue to utilize carbohydrates as the major source of energy during the prolonged periods of exercise. If this supply of carbohydrates, however, is depleted, the body begins to utilize proteins to generate energy. The amino acid utilization resulting from protein results in a depletion of essential amino acids in the plasma which can cause many detrimental effects, such as the loss of the ability to repair damaged tissue.

A desirable nutritional supplement would be one which causes the maintenance of blood volume and cardiac output, provides a readily available energy source, improves skin blood flow, increases the number of electrolytes, reduces breakdown of proteins, and decreases the time needed for repair of the body following strenuous exercise.

The patch of the invention is one which provides an athletic supplement to a subject. The athletic supplement prevents the adverse effects of physical exertion or environmental exposure. An athletic supplement that "prevents the adverse effects of physical exertion or environmental exposure" as used herein is one which achieves one or more of the following parameters: maintains carbohydrate levels in blood within the normal range, prevents loss of electrolytes below a normal range, or provides an energy enhancing amount of an energy enhancer in the plasma. A normal range of carbohydrates in the blood as used herein is that amount which during periods of extreme exercise is sufficient to prevent protein metabolism. That amount is within the range of 65–140 mg/dl. Preferably the amount is within the range of 80–120 mg/dl.

In one aspect the invention is a patch for topical delivery of an athletic supplement to a subject which includes at least two compounds selected from the group consisting of a carbohydrate, an electrolyte, a vitamin, an amino acid, a mineral, and an energy enhancer. The patch may also include other nutrients such as sodium chloride, potassium chloride, anhydrous magnesium sulphate, dodecahydrated disodium hydrogen phosphate, hydrated sodium dihydrogen phosphate, dextrose, sucrose, ascorbic acid, pyridoxine hydrochloride, sodium citrate, and citric acid.

The carbohydrate used in the patch may be a simple saccharide, a complex saccharide or a mixture thereof. Simple saccharides generally provide the most immediate energy source for the athlete. It is desirable, however, to include a mixture of carbohydrates to provide sustained energy source and to avoid fluctuations in serum glucose levels which occur as the result of ingestion of glucose. Complex saccharides are carbohydrate polymers which generally are approximately 5–10 monomeric units. These compounds are commercially available. The polymers are converted into simple carbohydrates in vivo by digestion, hydrolysis and host catabolic pathways. Dextrins, for example, are glucose polymers which are generally obtained by hydrolysis of starch and are available commercially from numerous sources.

Carbohydrates include sugars, monosaccharides, oligosaccharides, such as for example, N-acetyl-D-galactosamine, D-glucose (dextrose, corn sugar), D-glucosamine, N-acetyl-D-glucosamine, N-methyl-D-glucosamine, D-mannose, D-ribose, D-xylose, D-fructose, D-galactose, D-galactosamine, cellobiose, maltose, galactose, and sucrose. The carbohydrates may be in the form of monomers or polymers, e.g., glucose polymers, such as maltose or maltodextrin. The carbohydrate polymers are the preferred source of carbohydrate because they can be cleaved enzymatically in the body to supply a constant source of energy over a course of several hours.

The preferred amount of carbohydrates within the patch will vary depending on many factors such as the size of the patch and the type of activity that the patch will be used for. The actual amount of carbohydrates may range from 50 mg–100 g. A more preferred range is from 1–5 g.

The patch may also include electrolytes. Electrolytes in the appropriate quantities increase the efficiency of the body to utilize glycogen and improve muscle activities. Potassium is an extremely important source of electrolyte that is involved in sugar absorption in the gastrointestinal tract. Potassium deficiency is very common in athletes. The appropriate supplementation reduces physical and metabolic stress and improves performance. The best source of potassium is potassium chloride. It has been found that a significant amount of sodium is lost in sweat during prolonged exercise. If the sodium that is lost is not replenished, there is a contraction of plasma volume, a suppression of the thirst mechanism, and a loss in ability of distal renal tubules to resorb water.

Electrolytes are salts of a metal of the group I and II of the periodic system. Electrolytes include, for example, inorganic and organic salts of sodium, potassium, calcium and/or magnesium. Examples of these salts include sodium acetate, acidic sodium citrate, acidic sodium phosphate, sodium amino salicylate, sodium bicarbonate, sodium bromide, sodium chloride, sodium citrate, sodium lactate, sodium phosphate, sodium salicylate, sodium sulphate (anhydrous or Glauber's salt), potassium acetate, potassium bicarbonate, potassium bromide, potassium chloride, potassium citrate, potassium-D-gluconate, mono- and dibasic potassium phosphate, calcium acetate, calcium chloride, calcium citrate, calcium-D-gluconate, calcium lactate, calcium laevulinate, dibasic calcium phosphate, magnesium chloride and magnesium sulphate. Preferred electrolytes include sodium bicarbonate, sodium phosphate, potassium bicarbonate, potassium chloride, dibasic potassium phosphate, calcium carbonate and magnesium carbonate.

The actual amount of electrolytes present in the patch will vary depending on many factors described herein. In general, the electrolytes are present in the patch in amounts of 2–2500 mg and preferably in amounts of 5–1000 mg.

Vitamins may also be included in the patch. Vitamins are organic compounds required for the transformation of energy for regulation of the metabolism of structural units. Vitamins include, for example, vitamin A, vitamin D3, vitamin Z, vitamin E, folic acid, thiamine, riboflavin, niacin, vitamin B6, vitamin B12, biotin, pantothenic acid, and vitamin K1. Some of the vitamins included in the patch also function as antioxidants. These include, for example, β-carotene, vitamin C, vitamin E and selenium.

A particularly preferred type of vitamin which can be included in the patch is vitamin B-15. Vitamin B-15, also known as Russian B-15 or dimethylglycine (DMG), has been linked to the improved performance of many Soviet athletes. The physiological effects of vitamin B-15 are diverse and include at least the following: the ability to increase oxygen utilization by muscle, depress muscle glycolysis, spare glycogen and thus enhance endurance, prevent exercise-induced hypoglycemic fatigue by normalizing blood glucose during exercise, lower blood lactate during exercise (increased blood lactate has been associated with the onset of fatigue), activate lipid metabolism, and increase work tolerance). It is believed that DMG functions as a methyl donor by transferring methyl groups to compounds such as folic acid which cause the biosynthesis of important molecules.

The patch also includes amino acids or salts thereof. Muscle cells require both essential and nonessential amino acids to undergo protein synthesis. It is known that the branched amino acids, and leucine in particular, stimulate protein synthesis in at least some skeletal muscles and the liver. Skeletal muscle is the primary site for the initial step in the catabolism of branched amino acids, which is referred to as the oxidation resulting in energy production. The first step in the oxidative catabolism of branched amino acids is transamination, which is the enzymatic transfer of the α-amino group to another molecule. Transamination produces a branched ketoacid. The branched ketoacid formed by transamination can either accept an amino group to become a branched amino acid or can be irreversibly catabolized for calories. Strenuous exercise increases the oxidation of branched amino acids. During exercise, the branched amino acids are predominantly derived from muscle protein, causing increased amounts of protein degradation. The branched amino acids, in addition to providing energy, also remove lactate from muscle. In preferred embodiments the patch includes at least one branched amino acid. It is especially preferred for the patch to include amino acids when the patch is administered at the end of the exercise or after the exercise is complete. The administration of amino acids after exercise increases protein synthesis and reduces protein breakdown, thus improving net muscle protein balance. *Acta. Physiol. Scand.*, V. 162, p. 377–387 (1988).

Essential amino acids include isoleucine, leucine, valine, lysine, methionine, phenylalanine, threonine, and tryptophan. The nonessential amino acids include alanine, arginine, aspartic acid, glutamic acid, aminoacetic acid, histidine, proline, serine, tyrosine, and cysteine.

The actual amount of amino acid included in the patch will vary depending on the type of amino acid and other parameters discussed herein. Preferably the amino acids are present in a range of 5–250 mg.

Chromium may also be included in the patch. Chromium is a component of glucose tolerance factor (GTF) which potentiates the action of insulin. Chromium has been shown to increase lean muscle deposition in humans when administered as a supplement and also to increase glucose tolerance and insulin sensitivity. (Anderson, R. A., *Eur. J. Appl. Physiol.*, V. 63, p. 146 (1991)). When chromium is administered during exercise, it is believed to facilitate the interaction between insulin and insulin receptors on tissues such as muscle and fat. Thus, it is desirable to include chromium in the patch.

It is desirable in some embodiments to include pyruvate in the patch in order to enhance the energy stores available to cells. Even a small amount of pyruvate improves performance and endurance during athletic events because it enhances entrance of acetyl CoA into the Krebs cycle. The Krebs cycle, a biochemical pathway, provides a working muscle with energy source. Under normal conditions pyruvate is formed from glucose, but during periods of exercise not enough pyruvate can be generated from this source to supply the cells with energy. A loss of pyruvate also prevents metabolism of fats as an energy source because fats enter the Krebs cycle as acetyl CoA. Thus, as pyruvate concentration is decreased in the bloodstream, a loss of pyruvate as a direct energy source as well as the ability to utilize fat as an energy source is lost. Thus, by supplementing the blood with pyruvate, adequate energy supplies can be achieved.

During the period of exercise and recovery after exercise, the fast-twitch muscles produce lactic acid, which is then available for a fuel for slow-twitch, highly oxidative skeletal muscle fibers. Thus, lactic acid provides a more immediate fuel source than dietary glucose. Lactic acid is not a desirable fuel source for the body. U.S. Pat. No. 5,420,107, issued to Brooks, discloses a series of lactic acid-like substances which provide an immediate fuel source to athletes during exercise and recovery from exercise which augment the beneficial effects of dietary glucose and other carbohydrates. The patent teaches that at least one organic lactic acid salt in an amount sufficient to affect an mammal's fluid electrolyte or carbohydrate balance during exercise and/or subsequent recovery can be administered as a nutritional supplement. Such a supplement may also be added to the patch of the instant invention.

Although it is desirable to maintain concentrations of pyruvate within normal ranges, an excess of pyruvate should not be added. Lactate is derived directly from pyruvate during strenuous exercise which occurs in an anaerobic manner. Build up of lactate in the muscle can cause muscle fatigue.

The patch may also include a mineral. Minerals include but are not limited to trace elements, iron, magnesium, copper, zinc, manganese, selenium, molybedemum, chromium, and iodide.

The patch also may include ammonia neutralizers, which in general are amino acids, e.g., α-alanine, arginine, asparagine, cystine, cysteine, aspartic acid, glutamic acid, glutamine, glycine, histidine, α-hydroxylysine, hydroxyproline, lysine, 3-monoiodotyrosine, leucine, methionine, norleucine, phenylalanine, proline, threonine, serine, tyrosine, tryptophan and the salts thereof, e.g., potassium, magnesium, and the phosphate salts.

The patch may also include energy enhancers. As used herein an "energy enhancer" is a compound which stimulates muscular activity. Energy enhancers include, for example, vitamins of the vitamin B group, creatine, choline, and some branched chain amino acids. Vitamins of the vitamin B group include, for example, vitamin B1 (thiamine, aneurin), vitamin B2 (riboflavin), vitamin PP (niacinamide), vitamin B6 (pyridoxine), pantothenic acid, and L-carnitine. Choline include chloride and other forms of choline. Useful branched chain amino acids include, for example, leucine, valine, and isoleucine. Preferred quantities of vitamins of the vitamin B group are 10–500 µg. Preferred quantities of branched chain amino acids are 3–10 mg. Preferred quantities of the others are 500 mg. A preferred energy enhancer is a neuromuscular enhancer. Neuromuscular enhancers include, for example, choline (choline chloride), and higher saturated fatty alcohols, particularly $C_{25}$–$C_{30}$ fatty alcohols (e.g., octacosanol or cerotyl alcohol). Neuromuscular enhancers may be present in amounts of 1–2000 µg, or more preferably 3–20 µg and most preferably about 5 µg.

It is possible to include many of the components of the athletic supplement in multiple patches. For instance, one patch may contain the carbohydrate and another patch may contain a group of other compounds such as vitamins, amino acids, electrolytes, minerals, and energy enhancers. The use of multiple patches is advantageous for example when it is desirable to administer a large amount of some components, such as carbohydrates and smaller amounts of other components.

The amount of nutrients within the athletic supplement will vary depending on many factors. For instance, the amount and type of nutrients included in a particular athletic supplement will depend on the nature and duration of the exercise being performed by the subject, the size and weight of the subject, and whether the subject is using supplemental sources of nutrients, such as sports drinks. One goal of the patch of the invention is to administer nutrients such that homeostatic conditions are maintained during the athletic event. Therefore, it is desirable to administer nutrients in an amount which will replace those being depleted by the athletic event. Normal levels of various nutrients that are present in a subject in the resting state are well known in the art and are extensively described in Remington: *The Science and Practice of Pharmacy*, Alfonso R. Jennaro, Ed., 19th Ed., 1995, Mack Publishing Company, Easton, Pennsylvania. Many of the nutrients incorporated in the athletic supplement are described in chapter 65, entitled *Vitamins and Other Nutrients*, of Remington. Other nutrients are described in other chapters. Based on this disclosure as well as many other references, those of ordinary skill in the art would be able to determine the actual amount of particular nutrients which should be included in the patch of the invention in order to replace depleted nutrients during periods of exercise.

In one embodiment the patch includes the following components in the following amounts sodium chloride: 69.6 mg; potassium chloride: 288.0 mg; magnesium sulphate: 148.0 mg; sodium citrate: 120.0 mg; disodium hydrogen phosphate: 480.0 mg; sodium dihydrogen phosphate: 111.6 mg; ascorbic acid: 100.0 mg; pyridoxine hydrochloride: 25.0 mg; citric acid: 420.0 mg; sucrose: 2 gm; dextrose: 2 gm.

The patch replaces nutrients which are lost during physical exertion. It is particularly useful for a subject requiring sustained energy, such as an athlete, or a subject who undergoes physical exertion at work. A "subject" as used herein includes any mammal in which it is desirable to improve the supply of nutrients during strenuous exercise. Subjects include, for instance, humans, horses, and dogs.

The patch may be a transdermal patch, a sublingual patch or buccal patch. Preferably, it is a transdermal patch. In general, transdermal patches include an athletic supplement reservoir, which may optionally include a permeation enhancer and/or a matrix, an impermeable backing layer, on one side of the athletic supplement reservoir and an adhesive overlay which forms a boundary on the other side of the athletic supplement reservoir.

Transdermal patches have been described extensively in the art. For example, such devices include, but are not limited to, those described in U.S. Pat. Nos. 3,170,795; 3,598,122; 3,598,123; 3,731,683; 3,742,951; 3,814,097; 3,921,636; 3,972,995; 3,993,072; 3,993,073; 3,996,934; 4,031,894; 4,060,084; 4,069,307; 4,077,407; 4,201,211; 4,230,105; 4,286,592; 4,292,299; 4,292,303; 4,314,557; 4,379,454; and 4,568,343, each of which is hereby incorporated by reference in its entirety.

The term "transdermal delivery" as used herein refers to the transport of compounds across the epidermis, where the compound is absorbed in the blood capillaries. In particular transdermal delivery refers to the administration of an athletic supplement in a vehicle such as a liquid or solid filler, diluent, excipient, or solvent which is involved in carrying or transporting the athletic supplement across the skin into the body. A transdermal patch is a skin patch which includes the athletic supplement and which may be applied to the skin of the subject. Many types of materials and designs for the transdermal drug delivery have been extensively described, see e.g., D. Hsien, "Multiple Lamination for Transdermal Patches," *Controlled Released Systems Fabrication Technology*, v. 1, pp. 167–188 (1988).

In a preferred embodiment of the invention, the athletic supplement is transferred by diffusion, preferably in the presence of permeation enhancers. In other embodiments, the athletic supplement may be transferred from the transdermal patch by iontophoresis or electroosmosis. Iontophoresis is based on the transport of charged ions by coulombic attraction/repulsion in an electric field. In general, iontophoresis induces an increased migration of ions or charged molecules in an electrolyte medium in the presence of the flow of electric current. Many transdermal patches which utilize iontophoresis for transport of drugs have been described such as, for example, U.S. Pat. No. 5,527,797. Electroosmosis is based on the transport of solvent in an electric field. Electroosmotic delivery of proteins from transdermal devices is described in, for example, U.S. Pat. No. 4,940,456.

Preferably the transdermal patch is a passive diffusion patch. A "passive diffusion patch" as used herein is a transdermal patch which is arranged to deliver the athletic supplement across the skin by passive diffusion rather than utilizing an electric field. Preferably it includes an adhesive layer, a backing layer, and an athletic supplement matrix layer.

When the patch is a transdermal patch, it is applied to the surface of the skin preferably by a contact adhesive layer. The adhesive layer is one which is compatible with the drug and thus does not interact with it. Such materials are well-known in the art and are disclosed in many of the patents described above which are incorporated by reference.

An adhesive layer prevents excessive migration of the athletic supplement from the transdermal patch during storage. It allows, however, the athletic supplement to be released into the skin once the patch is applied. The adhesive layer should also stick securely to the skin once it is applied and also be removed with minimum discomfort.

In order to enhance the ability of the adhesive layer to attach to the skin, it may optionally contain a tackifier. Preferably, the tackifier is a polymer which is insoluble in water and composed of a monomer which contains partly or wholly a (meth) acrylic alkyl ester. Such types of polymers include, but are not limited to, acrylic, N-butyl-methacrylic copolymer (Primal N580NF, sold by Japan Acrylic Chemical Company, Ltd.), acrylic methyl, acrylic 2-ethylhexyl copolymer (Nikasol TS-6520, sold by Nippon Carbide Industries Company, Ltd.), polyacrylic acid (Jurymer AC-10LPH, sold by Nihon Junyaku Company, Ltd.), methacrylic copolymer L (Plastoid L50, sold by Rohm Pharma GmbH), and aminoalkylmethacrylate copolymer E (Plastoid E35L, Plastoid E35M, Plastoid E35H, all sold by Rohm Pharma GmbH).

Adhesives useful for applying transdermal patches to the skin of the subject can be prepared from many types of materials, such as polyacrylate, silicone, polyisobutylene, and styrene-butadiene copolymers. These types of materials, as well as others, are described in "The Handbook of Pressure Sensitive Adhesive Technology," Second Edition (1989), van Norstrand, Reinold, which is hereby incorporated by reference.

In one embodiment, the adhesive material is an acrylic adhesive including at least one polymer selected from homopolymers of acrylic esters, copolymers of two or more types of acrylic ester units and copolymers of acrylic esters and other functional monomers. Acrylic esters include, but are not limited to, butyl (meth) acrylate, pentyl (meth) acrylate, hexyl (meth) acrylate, heptyl (meth) acrylate, octyl (meth) acrylate, nonyl (meth) acrylate, decyl (meth) acrylate, etc. Functional monomers include, but are not limited to, monomers containing a hydroxyl group, such as hydroxyethyl (meth) acrylate, hydroxypropyl (meth) acrylate, etc. and monomers containing an amide group such as methacrylate, dimetheylmethacrylamide, etc.

Cross-linked acrylate based adhesives (Avery Chemical Division, Mill Hall, Pa.) are useful in some embodiments such as when a plasticizer-type enhancer is used. Examples of commercially available materials include Avery 2533 adhesive, AS-460HPX (both from Avery Chemical Division), Duro-Tak® 9852 (National Starch, Bridgewater, N.J.) and Gelva GE 1753 (Monsanto).

Silicone adhesives are one type of adhesive commonly used in transdermal delivery devices. Silicone adhesives which are useful for forming the adhesive layer include but are not limited to high molecular weight polydimethyl siloxanes or polydimethyl diphenyl siloxane that contain residual silanol groups on the ends of the polymer chains, such as those described in U.S. Pat. Nos. 5,232,702 and 4,906,169.

Polyacrylate adhesives can be made by copolymerizing one or more acrylate monomers or are also available commercially from a variety of sources.

Polyisobutelane adhesives are mixtures of high molecular weight and low molecular weight polyisobutelanes. Such mixtures have been described in the art, e.g., PCT/US91/02516.

The adhesive layer may be a single continuous layer across the entire surface of the transdermal patch.

Alternatively, it may cover the perimeter edges of the patch but not the area from which the athletic supplement is released A membrane separates the athletic supplement from the adhesive layer. This membrane preferably does not limit the flow of athletic supplement from the device into the skin. Therefore, the rate of permeation of the athletic supplement through the membrane is greater than through the skin. Microporous membranes which are useful for this purpose include polyethylene and polypropylene films, nylon, and nitrocellulose films. Many such membranes are commercially available, including Cotran® 9701, Cotran® 9711 (polyethylene membranes, 50 μmin thickness, with a void volume of greater than 10%, 3M Corporation, St. Paul, Minn.), Celgard K256 (Hoechst-Celanese, Charlotte, N.C., microporous polyethylene), Solupor® SP.03, and Solupor® 7P2.0 (microporous polyethylene films, pore size 0.1–5.0 microns, DSM Solutech, The Netherlands).

The athletic supplement may be incorporated into a matrix. The use of a matrix construction can allow a high rate of delivery of the athletic supplement without the need to add additional permeation enhancers. Patents such as U.S. Pat. No. 5,770,219 describe solid matrix systems for enhanced transdermal drug delivery. The patent describes matrices made from acetate-acrylate copolymers which have unexpectedly high rates of drug delivery. These acetate-acrylate copolymer materials are commercially available from a variety of sources including Monsanto Chemical Company (Gelva®, which is a vinyl acetate-acrylate copolymer resin solution 737, and Gelva® 788), and Morton Thiokol, Inc. (Mortstik 207A and Mortstik 607, which are acrylate copolymers).

The matrix material in which the athletic supplement is incorporated may be any type of material which is compatible with the drug, and may, for example, be a gel or a polymer. Some materials which are useful include natural and synthetic rubbers, other polymeric materials, mineral oil, and petroleum jelly.

The matrix may also contain additional materials such as stabilizers, dyes, pigments, fillers, tackifiers, and excipients. Such additional materials are well-known in the art of transdermal delivery devices. Fillers include, for example, inorganic powders, such as precipitated silicic acid anhydride; cellulose derivatives, such as sodium cellulose glycolate (sodium carboxymethylcellulose), methyl cellulose, hydroxyethylcellulose, hydroxypropylcellulose, hydroxypropylmethylcellulose, and synthetic polymers, such as polyvinyl alcohol and polyvinylpyrrolidone; gelatin, gums, and starch.

The backing layer is impermeable and defines the top of the transdermal delivery patch. The backing is occlusive because it prevents loss of the athletic supplement and/or enhancers to the environment. The backing layer may be prepared from any material which is impermeable to the athletic supplement and other components of the patch. It may be a single layer or may be composed of several different types of layers. Many polymers are useful for making backing layers, such as polyvinylchloride, polyvinylidene chloride, polyolefins, polyethylene, polypropylene, polyurethane, and polyesters. In addition to these materials, polyamides, metal vapor deposited films or sheets thereof, rubber sheets, films, expanded synthetic resin sheets, unwoven fabrics, fabrics, knitted fabrics, papers, and foils may also be used. The materials may be laminated, pigmented or metalized.

Although backing layers may be prepared directly from raw materials, they may also be obtained as films from commercial sources. For instances, 3M Corporation, St. Paul Minn.; Dow Chemicals, Midland, Mich.; Avery Specialty Tape Division, Plainsville, Ohio; and A.F. Packaging, Winston-Salem, N.C., all supply commercially available films which can be used for backing layers. One type of backing layer which is commercially available from 3M Corporation is the Scotch Pak 1000. The backing layer may be made from Scotch Pak® 1006 or 1009, which are skin colored aluminized polyester films of 50 μm in thickness. Another type of backing layer is 3M-1012 which is a transparent polyester film laminate. Each of these commercially available backing layers is sold by 3M Corporation.

Transdermal patches can be formulated so as to produce an occlusive area which traps sweat between the skin layer and the patch causing hydration of the skin which will facilitate movement of the athletic supplement across the skin. Patches which function in such a manner are described in U.S. Pat. No. 5,466,465.

Generally the transdermal patch includes a liner which is positioned adjacent to the surface of the adhesive layer and which is removed prior to application of the transdermal patch to the skin. The liner which is used to cover the adhesive backing during storage and to prevent a vaporative loss of the athletic supplement during storage may be made from any impermeable film. It may be made from the same material as the backing layer or it may also be a metal foil, Mylar® polyethylene terphthalate, siliconized polyester, fumed silica in silicone rubber, polytretrafluoroethylene, cellophane, siliconized paper, aluminized paper, polyvinyl chloride film, etc.

The patches are generally stored in pouches which will prevent contamination and prevent damage associated with environmental conditions such as light and dryness. Foil pouches are particularly useful. Many types of storage pouches are commercially available, such as those available from Lithotype Company (San Francisco, Calif.; polyethylene, surlyn), James River Corporation (San Leandro, Calif.; polypropylene metalized film), Ivers-Lee, a division of Becton-Dickinson (West Caldwell, N.J.; 305W, 406), Jefferson Smurfet (Alton, Ill.; acrylonitrile butadiene copolymer film laminate).

In addition to the standard layered polymeric patches described above, the patch of the invention may also be a hydrogel matrix patch. Hydrogel matrix patches in general include alcohol, water, reactive agent, and hydrophilic polymers. This matrix may be incorporated into the transdermal patch between the backing and the adhesive layer. Additionally, the layer may be a liquid reservoir instead of a matrix.

In order to increase the skin permeability of the athletic supplement which is administered by transdermal devices, the skin may be treated with various chemicals prior to administration of the transdermal device, or compounds such as permeation enhancers may be delivered concurrently with the athletic supplement through the device. "Permeation enhancers" as used herein increase the permeability of skin to a poorly skin permeating active agent. Many types of permeation enhancers have been described in the prior art. For instance, U.S. Pat. Nos. 4,299,826; 4,343,798; 4,046, 886; 4,130,643; 4,405,616; 4,335,115; 4,130,667; 3,903, 256; 4,379,454; 3,527,864; 3,952,099; 3,896,238; 3,472, 931; 4,637,930; 4,788,062; 4,746,515; 4,863,738; 4,863, 970; 5,053,227; 5,613,958; 5,641,504; 5,693,335; and 5,641,504, as well as Great Britain Patent Nos. 1,011,949 and 2,142,238A and Idson et al., "Percutaneous Absorption," *J. Pharm. Sci.* (1975), 64, pp. 901–924 all describe various types of permeation enhancers. The patch of the invention may include one or more permeation enhancers.

In particular, U.S. Pat. No. 5,641,504 describes a compound, glycerol monolineate (GMLO) which is effective in enhancing the permeation of compounds through body surfaces and in particular through the skin. GMLO enhances the permeability of compounds to allow them to be delivered at therapeutically effective rates with reasonably sized transdermal devices. The GMLO is coadministered with a compound such as a drug to the body surface through a transdermal device.

Various types of permeation enhancers are useful according to the invention. For instance, polar solvents, such as dimethylsulfoxide, decylmethylsulfoxide, dimethylformamide and dimethylacetamide; cycloalkanes, such as azacycloheptan-2-one and 1-dodecylazacycloheptan-2-one; esters of carboxylic acids and alcohols, such as isopropyl, myristate and isopropyl palmitate; glycols; surface active agents, such as sodium laurylsulfate and sodium dodecylsulfate; derivatives of fatty acids, pyroglutamic acid and urea; and derivatives of amino acids having the formula $R^1NH—R^3—COOR^2$ wherein $R^1$ is a hydrogen atom, an acyl group having 1–20 carbon atoms or a hydrocarbon group having 1–20 -carbon atoms, $R^2$ is a hydrogen atom or a hydrocarbon group having 1–20 carbon atoms, and $R^3$ is $CH—R^4$ or phenyl, wherein $R^4$ is H, CH3, isopropyl group, 2-methylpropyl group or 1-methylpropyl group. Amino acid derivatives are described in U.S. Pat. No. 5,413,794 and are a preferred type of permeation enhancer. Ethanol has been found to increase the solubility of drugs up to 10,000-fold and to yield a greater than 100-fold flux increase in drugs and thus also a preferred permeation enhancer.

Permeation enhancers may be plasticizer-type enhancers or solvent-type enhancers. Both types of enhancers can be used together. A plasticizer-type enhancer generally is a fatty acid or fatty alcohol that is capable of increasing the permeability of a compound to the stratum corneum. The plasticizer-type enhancers migrate into the stratum corneum layers of the skin and enhance migration of the compounds within the transdermal patch into the skin by increasing the mobility and/or solubility of the compound within the skin. Solvent-type enhancers are hydrophilic compounds having molecular weights of about 200 or less which increase the permeability of drugs to the stratum corneum. These types of enhancers produce high flux rates of the compound within the transdermal device. When plasticizer enhancers and solvent-type enhancers are used together, a synergistic effect is achieved which results in a high delivery rate of compound across the skin barrier. Many types of plasticizer enhancers and solvent-type enhancers are described in detail in U.S. Pat. No. 5,613,958, which is hereby incorporated by reference.

Some plasticizer type permeation enhancers such as unsaturated fatty acids function by disrupting the lipid bilayer causing an increase in the solubility of lipid bilayers. Fatty acids, which are useful as permeation enhancers, and which disrupt lipid bilayers, include linoleic acid, capric acid, lauric acid and neodecanoic acid. The permeability enhancement of permeation enhancers for each compound to be transported can be calculated according to $\epsilon_{e/pg}=P^{e/pg}/P^{pg}$. $P^{e/pg}$ is the drug permeability from the enhancer/propylene glycol formulation and $P^{pg}$ is the permeability from propylene glycol alone. A more comprehensive list of lipid bilayer disrupting agents is described in European Patent Application No. 043,738 (1982).

Many patents have described permeation enhancers which are solubility enhancers. These patents include, for instance, U.S. Pat. Nos. 4,537,776; 4,973,468; 4,820,720; 4,863,970; and 5,006,342, as well as Great Britain Patent Application No. 2,153,223A and European Patent Application No. 043,738.

In addition to the permeation enhancers described above, U.S. Pat. No. 4,865,848 describes a novel type permeation enhancer which is sucrose monolaurate. This sucrose ester can be dispersed within the matrix along with the active agent.

Various preservatives may also be used to stabilize the athletic supplements contained within the transdermal patch. The type of preservative selected will depend on the type of components used within the athletic supplement as well as the matrix and other materials of the patch. Preservatives include, but are not limited to, alcohols, e.g., ethanol or isopropanol; quatrinary ammonium surfactants, as well as many other preservative compounds known in the art. *The United States Pharmacopeia XXI* 1985 includes a section which describes parameters for selecting compounds useful in enhancing the stability of various drugs (pp. 1345–1347). Other factors, such as pH and ionic strength of the solution, also influence the stability of the compounds within the athletic supplement.

Another preferred dosage form is a sublingual tablet. Preferably, the sublingual tablet disintegrates and releases the athletic supplement to the sublingual mucosa within a ten minute period of time and most preferably within five minutes.

The patch of the invention is designed to deliver the athletic supplement for an extended period of time of a week or longer. Preferably, the athletic supplement is released within a period of 24 hours or less. It is desirable to have the athletic supplement be released during the period of the athletic event and any recovery period. Patches may be designed which release the athletic supplement for various periods of time, such as 12 hours, 8 hours, 6 hours, 4 hours, or 2 hours. The type of patch used will depend upon the particular athletic event and other parameters, such as whether nutrients are obtained through other means.

In some embodiments, it is desirable to apply the patch before or at the start of the athletic event. If the patch is the primary source of athletic supplement during the event, then preferably the patch will include at least one carbohydrate, chromium, and an energy enhancer. If an additional athletic supplement is being administered, such as a sports drink, the patch will preferably include a mixture of components that are not found within the sports drink or for which it is desirable to administer a higher quantity of the nutrient. In other embodiments, it is desirable to apply the patch during the course of the athletic event. For instance, when an additional athletic supplement, such as a sports drink or sports bar is administered prior to the athletic event, then it may be desirable to apply the patch at a later time period to supplement the nutrients that are being lost. At any point, the patch may be used in combination with sports drinks or sports bars or other types of athletic supplements. In another embodiment, the patch may be applied near the end of the exercise or after the exercise has been completed. It may be desirable to do this to prevent cellular damage caused by a loss of nutrients. For instance, it has been demonstrated that there is an increase in leucine oxidation during exercise which results in an increased net protein breakdown. The administration of amino acids through the patch after exercise helps to increase protein synthesis and prevent breakdown to result in a net improvement in muscle protein balance. Thus it is particularly preferred that a patch which is to be used after exercise is complete includes amino acids.

The rate of release of the athletic supplement and any permeation enhancers from a passive diffusion patch may be controlled in a variety of means. For instance, the matrix material in which the athletic supplement is incorporated may be manipulated to control the speed with which the athletic supplement is released. Additionally, the transdermal delivery device may include a rate controlling membrane which controls the release rate further. Rate controlling membranes may be prepared from permeable, semipermeable, or microporous materials. Such materials are well-known in the art for controlling the delivery of drugs. The materials may be prepared from, for example, polyethylene, polyvinyl acetate, and ethylene vinyl acetate copolymers.

U.S. Pat. No. 5,656,286, which is hereby incorporated by reference in its entirety, describes an improved pressure sensitive adhesive composition which is suitable as a matrix for controlled release of a drug and which is composed of a blend of a rubber based pressure sensitive adhesive and a soluble polyvinylpyrrolidone (PVP). A pressure sensitive adhesive is a viscoelastic material which adheres to substrates with only slight pressure and remains tacky. It was described in the patent that the transdermal permeation rate of a compound could be controlled by selectively modulating the solubility of the compound. The transdermal permeation rate means the rate of passage of the drug through the skin. The solubility parameter is the sum of all the intermolecular attractive forces which are related to the mutual solubility of the compounds. Many methods are known for determining solubility parameters. The permeation rate is controlled by altering the differences in the solubility parameters of the adhesive material versus that of the compounds within the athletic supplement. These manipulations are well-known in the art and in particular described in U.S. Pat. No. 5,656,286.

U.S. Pat. No. 5,466,465 describes the use of a visible indicator for which changes in color indicate the status of the athletic supplement within the patch. For instance, the indicator may display one color when the patch contains a significant amount of athletic supplement, but as the amount is depleted, the color changes to indicate that depletion. The use of the visual indicator can be of help to the subject to determine whether it is necessary to apply an additional patch during the athletic event. The entire contents of U.S. Pat. No. 5,466,465 are incorporated herein by reference.

The transdermal patch may be of any shape, such as oblong, square, round, rectangular, etc. The transdermal patch may also have a variety of sizes. The total surface area in general may range from 1–400 $cm^2$. The actual surface area will depend upon a number of factors, including the amount of athletic supplement to be delivered over a specified period of time, and the presence or absence of permeation enhancers as well as the type of adhesive layer and membrane material. When patches are greater than 100 $cm^2$, it is preferred that the adhesive layer does not cover the entire surface of the patch, to reduce irritation of the skin. In some cases, it is preferred to use textile fabrics for larger patches.

U.S. Pat. No. 5,473,966 describes a method for sizing transdermal patches. The method is useful for reducing the size of the patch, and thus the amount of active ingredient within the patch which will be administered. The method can be used to customize patches for release profiles of the athletic supplement over specific periods of time. For instance, if a subject were using a 50 $cm^2$ patch and desired to use one third less athletic supplement, it would be possible to reduce the patch area to 33 $cm^2$ following such a method, or using any such method known in the art.

The transdermal patch may be a standard single compartment patch or in some embodiments it may be a multi-compartmentalized patch, such as those described in U.S. Pat. No. 4,666,441. Multi-compartmentalized patches are useful, for example, for differentially regulating the components within the athletic supplement and how they are administered. For instance, it may be desirable to consistently administer a carbohydrate throughout the entire athletic event, but to only administer electrolytes and vitamins during later periods, once the supply of these nutrients has become depleted. This can be accomplished by including the carbohydrate within one compartment of the transdermal patch within a matrix which will allow for the continuous administration over the entire time period and by incorporating the other components within a different compartment which is designed to release the components after a specified time period. Means for controlling the time for release of components from transdermal patches is well-known in the art, and may be accomplished, for instance, by including an additional layer of matrix which must be dissolved first before the athletic supplement can begin to permeate across the skin.

The patch of the invention provides all of the nutritional, carbohydrate, and energy requirements of an athlete under conditions of physical stress without causing gastrointestinal disturbances. In general, athletes experience athletic stress when their metabolic rate exceeds approximately 500 kcal per hour as a result of physical exertion, or, alternatively, when through sustained exertion a pulse rate of 125 beats per minute or higher is maintained for a period of 90 minutes or more. Under such conditions, supplemental nutrient sources are required. Additionally, under conditions of physical exertion there is an increased use of amino acids from muscle tissue as an energy source, and an increased percentage of total calories are supplied by the direct oxidation of the branched chain amino acids, leucine, isoleucine, and valine. (K. G. Schott, et al., "On the Role of Branched-Chain Amino Acid in Protein Metabolism of Skeletal Muscle," *Journal of Z Naturforsch*, May–June 1985, pp. 427–437; S. F. Lowry, et al., "Influence of Nutritional Status on Exertion Induced Four Arm Amino Acid Metabolism in Normal Man," *Journal of Surgical Research*, May 1984, Vol. 36, pp. 438–445, and A. E. Harper, et al., "Branched-Chain Amino Acid Metabolism," *Annual Review of Nutrition*, 1984, Vol. 4, pp. 409–454). The breakdown of muscle protein during such conditions can be assessed by the presence of nitrogen in urine. If branched chain amino acids are administered during exercise, loss of nitrogen is not detected.

The ability of a patch of the invention to counteract the physiological effects of physical exertion such as the breakdown of muscle protein or loss of other important nutrients can be assessed in several ways. For instance, the effect of the patch may be assessed by using conventional experimental parameters to measure the percent of the components which enter the bloodstream and which are present during the prescribed time period, such as during the athletic event. Quantitative analysis can be assessed by isolating blood samples at various time points after the patch has been applied and measuring the amount of nutrients in the blood. A normal range of parameters includes serum bicarbonate (24–26 mEq/L), serum potassium (3.5–5.3 mEq/L), serum chloride (96–106 mEq/L), serum uric acid (3–9 mg/dl), serum phosphorus (2.5–4.5 mg/dl), and lactate (0.1.6 mEq/L), sodium (135–147 mEq/L), urine pH (5.1–9.0). An in vitro quantitative assay is provided in the Examples below. This assay is useful for assessing the appropriate amounts of nutrients which should be included in a particular patch.

Alternatively the effect of the patch can be assessed using qualitative measures reported by the subject wearing the patch. That is, the patient may decide whether the patch has beneficial effects during the period of exertion. These types of qualitative assessment tests have been used successfully to evaluate many types of treatments for chronic illnesses as well as addictions. The simplest form of qualitative analysis involves the use of a nutrient patch for some experimental subjects and placebos for others. Each subject determines whether the treatment improved, worsened or made no change in their ability to withstand strenuous exercise.

The amount of athletic supplement present in the patch depends on several factors, such as the desired time frame for release of the athletic supplement, the anticipated intensity of the athletic event, the particular components within the athletic supplement, the permeability of the matrix and adhesive layer. In a preferred embodiment, the athletic supplement is present in the matrix at approximately 0.01–20% athletic supplement, 50–90% matrix, i.e., polymer, and 1–70% permeation enhancer. In some cases, a secondary permeation enhancer may also be included.

EXAMPLES

Example 1

Preparation of a Transdermal Patch

Many techniques are well-known in the art for preparing transdermal patches from each of the above-described components. One method referred to as the form-fill-seal technology is performed using layering techniques. The adhesive is layered onto the liner, and then the membrane material if present is affixed to the adhesive. The athletic supplement is incorporated into a reservoir and dispersed either on the backing or the membrane, and then the backing is sealed to the membrane. Many other methods are well known in the art. The patches of the invention can be prepared by any such method.

The athletic supplement is mixed and in some cases sonicated with or without a skin permeation enhancer. For instance, a mixture of free amino acids may be dry blended to produce a fine amorphous uniform powder, which generally should be accomplished at around 40° C. and using blending. The mixture should be blended for at least 1 minute and preferably between 2 and 5 minutes. The blending may be accomplished using a powder mill, such as a Waring Model No. 34BL22 blender. A suitable copolymer resin, such as Monsanto GELVA® 737 vinyl acetate acrylate copolymer resin adhesive solution is then added to the athletic supplement mixture and rotated for an extended period of time. The athletic supplement mixture is then cast on a polyester film to about 100 micrometers in thickness. The solvent in the polymer system is evaporated under high temperature such as 75° C. in a forced air oven. The resultant athletic supplement reservoir matrix is then laminated with a backing layer film.

Example 2

Single and Multi-Compartmentalized Patches

An example of a transdermal patch of the invention is shown in FIG. 1. The patch of FIG. 1 includes a diffusion matrix layer that uses a reticulated macroporous polymeric foam as a framework for holding a viscoelastic athletic supplement-polymer mixture. The patch, 10, is a four-layer, laminated composite that is adapted to be adhered to the skin. The outermost layer, the backing layer, 12, functions as the primary structural element of the device and also serves as a protective covering to prevent the athletic supplement from being transmitted from the device via the outermost surface. The backing layer, 12, preferably is made from a sheet or film of a resilient elastomer, such as those described above, of about 10–75 microns in thickness.

The athletic supplement-containing matrix layer, 14, functions as a reservoir for the athletic supplement, a permeation enhancer, and optionally a pressure sensitive adhesive. The framework of the matrix is a reticulated macroporous polymeric foam, 16. Preferably, the network is essentially completely open pores (90% or greater). The pore rating of the reticulated foam will normally be in the range of about 10–40 pores per linear centimeter and the density (unfilled) will typically be in the range of about 0.01–0.5 g/cm$^3$. As described in more detail above, the polymer is useful for such foam frameworks may be manufactured from polyurethanes and polyethylenes.

A pressure sensitive adhesive layer, 18, covers the exposed face of the matrix layer, 14. A release liner, 20, covers the other side of the pressure sensitive adhesive. The pressure sensitive adhesive layer, 14, is generally a medical grade adhesive composition having a thickness on the average of 25–100 microns. Useful materials for forming the adhesive are described above, and include for instance polydimethylsiloxane.

The pores of the foam may be wholly or partially filled with a viscoelastic hydrophobic athletic supplement-permeable polymer and an enhancer. The polymer, as described above, acts as a carrier for the athletic supplement. The enhancer functions to control the solubility of the athletic supplement in the polymer and/or absorption into the skin. The hydrophobic polymer renders the device water resistant and prevents liquid water from being absorbed by the device, thereby increasing its functionality and wearability.

Figure 2:
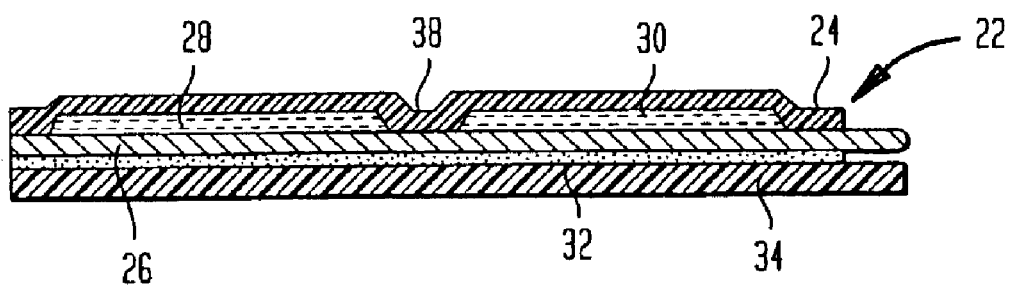
FIG. 2 shows a multi-compartmentalized transdermal patch.

A multicompartmentalized patch is shown in FIG. 2. The patch of FIG. 2 also is a four-layer composite but defines at least two separate compartments for containing the components of the athletic supplement. One compartment contains, for instance, some of the components such as the carbohydrate, and the other compartment contains other components such as vitamins and electrolytes. The patch, 22, has a backing layer, 24, sealed to a rate controlling membrane, 26, in a manner to create two chambers, the first athletic supplement containing chamber, 28, and the second athletic supplement containing chamber, 30. An adhesive layer, 32, covers the rate controlling membrane and a release liner, 34, covers the adhesive layer.

The multicompartmentalized patch may be prepared by the following method. A silanized polyester (or other suitable material, described above) approximately 75 microns thick is used as release sheet, 34. The adhesive layer, 32, is cast onto the release sheet, and may be for example polyisobutylene. The adhesive layer is then laminated to the rate controlling membrane, 26, which may be about 100 microns thick. Next, the materials which will become the contents of the athletic supplement containing chambers 1, 28, and 2, 30, are placed in separate areas on the rate controlling membrane, 26. Finally, a suitable backing layer, 24, having a heat sealable coating on one surface is placed over the two areas which are to become chambers 28 and 30, and the device is heat sealed, 36, around the parameter and between the two areas to form the two chambers, 28, and 30.

Referring to FIG. 1 which illustrates an exemplary transdermal patch of the invention, the backing sheet 10 is a lightweight pliable strip which covers an entire surface of the transdermal patch. The backing sheet 10 covers the active agent reservoir 12 on one surface. On the other surface of the reservoir, the adhesive layer 14 covers the reservoir. A protective undercoating 16 is positioned adjacent to the adhesive layer. The protective undercoating is removed prior to contacting the adhesive layer with the skin.

Example 3

Quantitative Assay of Release of Nutrients from a Transdermal Patch

A modified Franz flow-through cell system can be used for in vitro penetration studies to determine the efficiency of the particular matrix at delivering the athletic supplement. One of the polyester layers is peeled off of the athletic supplement matrix layer. The athletic supplement matrix layer is then pressed onto the stratum corneum of human cadaver skin membrane. This skin membrane with the backing and matrix affixed thereto is then mounted between two half cells and fastened with a clamp. The receiver compartment is filled with 0.1% gentamycin in distilled, deionized water, and the temperature is maintained at 32° C. Samples are taken at preset intervals and assayed by HPLC or other known assays. The type of assay depends on the component within the athletic supplement to be identified. The flux is then calculated from the slope of the cumulative amounts of the athletic supplement in the receiver compartment versus time.

Example 4

Preparation of a Sublingual Tablet

One method for preparing sublingual tablets is described below. In the example sublingual tablets are made in accordance with the formulation set forth in Table 1 and Table 2 below.

TABLE 1

| | |
|---|---|
| Branched chain amino acids | 10 mg |
| Mannitol, USP (DC grade) | 31.5 mg |
| Microcrystalline, Cellulose | 40.35 mg |
| Sodium Starch Glycolate NF | 2.6 mg |
| Sodium Saccharin, USP | 0.5 mg |
| Flavor S.D. Peppermint, FCC | 0.75 mg |
| Magnasweet MM 188M | 0.5 mg |
| Vanilla flavor #800 | 0.2 mg |
| D&C Yellow #10, Aluminum Lake | 0.2 mg |
| Magnesium stearate, NF | 0.5 mg |
| Aerosil 200 | 0.4 mg |
| TOTAL | 80 mg |

TABLE 2

| | |
|---|---|
| Branched chain amino acids | 5 mg |
| Vitamin C | 5 mg |
| b-carotene | 0.20 mg |
| Choline | 0.02 mg |
| Octacosanol | 0.02 mg |
| Vitamin B | 0.50 mg |
| Mannitol | 30.30 mg |
| Microcrystalline cellulose (FMC) 4.00 | 34.00 mg |
| Sodium starch glycolate (EXPLS TAB Mendell) | 2.60 mg |
| Magnesium stearate NF | 0.50 mg |
| Colloidal silicon dioxide (Aerosil 200) | 0.40 mg |
| Sodium saccharin (Mallinckrodt) | 2.00 mg |
| Aspartame (Neutrasweet) | 4.00 mg |
| Peppermint (Virginia Dare HF82 SD #517) | 0.40 mg |

TABLE 2-continued

| | |
|---|---|
| Vanilla (Virginia DAre 800 NAT) | 0.30 mg |
| MAFCO Magnasweet 188M | 0.25 mg |
| Prosweet #560 (MM54) | 0.75 mg |
| Chocolate Flavor #682 | 2.00 mg |
| D&C Yellow #10 | 0 mg |
| TOTAL (mg) | 85.00 mg |

The formulations set forth in Tables 1 & 2 represent examples of sublingual tablet formulations. Individuals skilled in the art will recognize that modifications to the formulation can be readily made.

In the above formulation, mannitol, sodium saccharin, peppermint, magnasweet, vanilla, aspartame, prosweet, and chocolate are flavoring agents which are capable of masking the bitter taste of some of the nutrients such as the branched amino acids. The flavoring agents may be deleted without sacrificing efficacy. However, the sublingual tablet may have an unappealing taste. Flavorings may be altered to suit individual needs and tastes.

D&C yellow is used as a colorant. The colorant may be readily deleted or substituted with other dyes.

Magnesium stearate and Aerosil-200 are lubricants to release the tablet from press equipment. These ingredients may be substituted or deleted entirely depending on the manufacturing process.

Microcrystalline cellulose, mannitol and sodium starch glycolate provide the tablet core. The cellulose and starch facilitate binding the core ingredients and facilitate tablet disintegration in the presence of moisture. The relative amounts of these ingredients may be altered to adjust the disintegration of the tablet.

Quantities of all ingredients are weighed and all the ingredients, other than mannitol, are passed through a 80 mesh stainless steel sieve. The materials are blended in a suitably sized polythene bag for about five minutes and transferred to suitable blender, such as a PK Blender. The required quantities of mannitol are passed through a 40 mesh stainless steel sieve and added to the PK Blender with the other ingredients. The mixture is blended in the PK Blender for 10 minutes and unloaded. A sample of the blend is subjected to inspection for potency and other quality determining criteria. The bulk density is determined on the blend using bulk density apparatus set for 100 taps. The tablet press is set for the designated punches and the blend is compressed at 80 mg tablet weight.

The sublingual tablets are administered by placing a tablet under the tongue. The tablet is allowed to disintegrate and release the athletic supplement which is absorbed by the sublingual mucosa.

Example 5

Qualitative Analysis of a Patch

An assay for qualitative analysis of a combination of transdermal patches and sublingual tablets of varying strength is described. Sublingual tablets and transdermal patches are prepared in accordance with Examples 1 and 4. A placebo sublingual tablet and transdermal patch are formed by incorporating an inert material. These tablets and patches are administered to subjects just prior to or during strenuous exercise. A preferred method is to apply a transdermal patch to a subject prior to the start of the exercise and to administer a sublingual tablet during the exercise after the depletion of nutrients has begun.

The subjects are asked to evaluate various parameters of their well being throughout the course of the exercise. For instance, each subject assesses their general energy level, endurance, athletic performance and fatigue on a numerical 0–4 scale. The results are assessed for each athlete using various combinations of patches, sublingual tablets, or placebo under similar exercise conditions on different days.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of he invention are not necessarily encompassed by each embodiment of the invention.

All references, patents and patent publications that are recited in this application are incorporated in their entirety herein by reference.

We claim:

1. An article of manufacture, comprising:

a patch for topical delivery of an athletic supplement to a subject which includes an amino acid, chromium and a vitamin, and wherein the patch includes an athletic supplement reservoir housing the athletic supplement and a permeation enhancer, an impermeable backing layer on one side of the athletic supplement reservoir and an adhesive overlay on the other side of the athletic supplement reservoir.

2. The article of claim 1, further comprising an energy enhancer.

3. A method of administering nutrients to a subject comprising: transdermally administering an athletic supplement in an article of manufacture according to claim 1 to a subject while the subject is undergoing a physical activity to provide the subject with nutrition and energy required to perform the physical activity.

* * * * *